United States Patent [19]

Brtnik et al.

[11] Patent Number: 4,482,486

[45] Date of Patent: Nov. 13, 1984

[54] ANALOGS OF VASOPRESSIN

[75] Inventors: František Brtnik, Prague; Tomislav Barth, Roztoky; Pavel Hrbas, Prague; Karel Jošt, Prague; Ivan Krejči, Prague; Běla Kupkova, Prague; Alena Machova, Prague; Linda Servitova, Prague; Jana Skopkova, Prague, all of Czechoslovakia

[73] Assignee: Ceskoslovenska akademie ved, Prague, Czechoslovakia

[21] Appl. No.: 486,863

[22] Filed: Apr. 20, 1983

[30] Foreign Application Priority Data

Apr. 20, 1982 [CS] Czechoslovakia ............... 2803-82
Nov. 19, 1982 [CS] Czechoslovakia ............... 8301-82

[51] Int. Cl.³ .................... C07C 103/52; A61K 37/00
[52] U.S. Cl. .............................. 260/112.5 R; 424/177
[58] Field of Search ................. 260/112.5 R; 424/177

[56] References Cited

U.S. PATENT DOCUMENTS 3,446,789  5/1969  Rudinger et al. ............ 260/112.5 R
3,497,491  2/1970  Zavrol et al. ................ 260/112.5 R
4,399,125  8/1983  Manning et al. ............. 260/112.5 R

OTHER PUBLICATIONS

Barth, et al., Collection Czechoslov. Chem. Commen. (1974) 39, 506–508.
Hechter, et al., The Journal of Biological Chem. 253, No. 9, (1978) 3230–3237.
Schröder, et al., The Peptides II, (1966) 372,373.

Primary Examiner—Delbert R. Phillips

[57] ABSTRACT

Vasopressin analogs of the formula

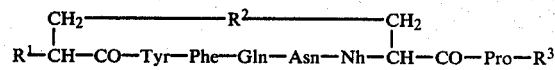

wherein
$R^1$ is H, $R^2$ is $CH_2S$ and $R^3$ is D-Arg,
$R^1$ is $NH_2$, $R^2$ is S—S and $R^3$ is D-Arg or L-Orn are described. The described analogs resist enzymatic cleavage while retaining their effect on the central nervous system. These compounds lack a glycinamide residue in the 9 position and have the L-arginine in the 8 position replaced with its stereoisomeric form or with an ornithine residue. The compounds evidence little or no peripheral endocrine effects of natural vasopressin.

4 Claims, No Drawings

ANALOGS OF VASOPRESSIN

This invention relates to vasopressin analogs, more particularly, the present invention relates to analogs of vasopressin from which the glycinamide residue has been removed from the 9 position. The described analogs are stabilized against enzymatic cleavage and evidence significant effects on the central nervous system.

Heretofore, it has been known that neurohypophysical hormones and certain analogs thereof affect the memory, sleeping characteristics and learning of experimental animals (D. de Wied: Proc. Roy. Soc. B 210, 183 (1980)). However, for practical applications of such compounds it is necessary that these compounds do not exhibit the endocrine activity of natural hormones as well as being protected against enzymatic cleavage.

In accordance with the present invention, these requirements are successfully met by appropriate modification of the natural hormones. Thus, it has been discovered that the removal of the glycinamide residue in position 9 and replacement of L-arginine in position 8 with the stereoisomeric form or with the ornithine residue yields the desired characteristics. In an alternative embodiment the disulfide linkage may be replaced with a thioether linkage.

The analogs described herein are of the formula

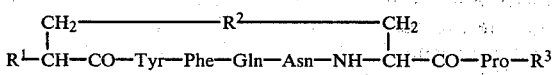

wherein the substituents are as follows:
where
$R^1$ is H, $R^2$ is $CH_2$-S and $R^3$ is D-Arg,
where
$R^1$ $NH_2$, $R^2$ is S-S and $R^3$ is selected from among D-Arg and L-Orn and all other chiral amino acids belong to the L-series.

In the above-identified formula, the designations set forth represent the following:
Try=tyrosyl,
Phe=phenylalanyl,
Gln=glutaminyl,
Asn=asparaginyl,
Pro=prolyl,
D-Arg=D-arginine, and
L=Orn=L-ornithine.

For purposes of exposition, compounds of formula (I) are designated as follows:
I (a) $R^1$=H, $R^2$=$CH_2$-S, and $R^3$=D-Arg
I (b) $R^1$=$NH_2$, $R^2$=S-S, and $R^3$=D-Arg
I (c) $R^1$=$NH_2$, $R^2$=S-S, and $R^3$=L-Orn The endocrine biological activities (in I.U./mg—International Unit—see "Handbook of Experimental Pharmacology", Vol. XXIII: Neurohypophysical hormones and similar polypeptides (B. Berde, Ed), p. 131, Springer-Verlag, Berlin 1968) of the described compounds were determined in rats.

The results are set forth in Table I below together with the values of natural hormone arginine vasopressin for comparative purposes.

TABLE I

| Com-pound | Uterotonic | Galactogogic | Pressor | Antidiuretic a | b |
|---|---|---|---|---|---|
| Ia | 0.09 | — | inhibition | 0.8 | 0.2 |
| Ib | 0.07 | 0.12 | 0.2 | 4.5 | 0.4 |
| Ic | 0.09 | 0.02 | 0.2 | 0.3 | 0.1 |
| AVP[c] | 17 | 69 | 465 | 465 | 20 | a = anaesthesized rat
b = non-anaesthesized rat Activity is expressed in percent of the effect of [8-D-argine] deaminovasopressin at the level of threshold efficiency
[c] = [8-arginine] - vasopressin As noted from the data in TABLE I, the uterotonic, galactogogic and pressor activities of the compounds of the invention are three orders of magnitude or lower than the corresponding activity of the natural hormone. Similarly, the antidiuretic properties of the compounds is at least two orders of magnitude lower than the activity of the natural hormone.

The described analogs were employed in the test of the passive defense reaction, the so-called passive avoidance, wherein the desirable effects of natural vasopressin on memory processes were proven. The underlying principle of the test is that the experimental rats avoid the area in which they receive moderate electrical shock upon their paws. The length of the period of avoidance is evaluated. If the administered compound extends this reaction, the effect may be interpreted as strengthening the memory trace as it relates to the experimental situation. The compounds were administered in a dose of 5 $\mu g.kg^{-1}$ subcutaneously immediately after introducing shock into the paws of the animals or 20 hours before the test for retention of the avoidance reaction. In light of the fact that the affect is present 20 hours after application, it is evident that the affect of the analogs is of lengthy duration.

Analysis of amino acids was conducted with an automatic device (Development Workshops, Czechoslovak Academy of Sciences, type 6020). Samples of peptides were hydrolyzed in 6M HCl at 105° C. and 150 Pa for 20 hours. Thin-layer chromatography was then performed on silica gel plates in the following systems:
S1:2-butanol—98% HCOOH—$H_2O$ (75:13.5:11.5)
S2:2-butanol—25% $NH_4OH$—$H_2O$ (85:7.5:7.5)
S3:1-butanol—$CH_3COOH$—$H_2O$ (40:10:10)
S4:1-butanol—$CH_3COOH$—pyridine—$H_2O$ (15:3:10:6)
S9:benzene with 20% methanol
S13:1-butanol—$CH_3COOH$—$H_2O$ (50:15:40)
S23:ethyl acetate—pyridine—$CH_3COOH$—$H_2O$ (5:5:1:3)

Electrophoretic analysis was carried out on paper Whatman 3 MM in a wet chamber at a potential gradient of 20 V/cm. The compounds were detected with ninhydrin or by the chlorination method.

The analogs of the invention may conveniently be prepared as described in the exemplary embodiment which follows. It will be appreciated that these examples are set forth solely for purposes of exposition and are not to be construed as limiting.

EXAMPLE 1

Preparation of compound Ia
Preparation of starting compounds (intermediates)
Preparation of benzyl ester of o-nitrobenzenesulfonylprolyl-$N^G$-p-toluenesulfonyl-D-arginine
A solution of 2.5 grams of 2,4,5-trichlorophenyl ester of o-nitrobenzenesulfonylproline and 2.5 grams of the hydrobromide of benzyl ester of $N^G$-p-toluenesulfonyl-D-arginine in 5 ml of dimethylformamide was stirred for 40 hours at laboratory temperature. Dimethylformamide was then evaporated in vacuum, the residue dissolved in ethyl acetate and the ethyl acetate solution extracted with a saturated solution of sodium hydrogencarbonate, water, a solution of $KHSO_4/K_2SO_4$ of pH 2 and water. After drying over $MgSO_4$, evaporation of ethyl acetate and crystallization from ethyl acetate and petroleum ether, 3 g (90%) of the product was obtained which melted 90°–92° C.; $[\alpha]_D -40.4°$ (c 0.4, methanol); $R_F$ 0.88 (S1), 0.75 (S2), 0.75 (S3), 0.83 (S4), 0.60 (S9). For $C_{31}H_{36}N_6O_7S_2$ (668.8) calculated: 55.67% C, 5.43% H, 12.56% N, 9.59% S; found: 55.92% C, 5.38% H, 12.68% N, 9.38% S.

Preparation of benzyl ester of the lactam of tyrosyl-phenylalanyl-glutaminyl-asparaginyl-S-(γ-carboxypropyl)cysteinylprolyl-N$^G$-p-toluenesulfonyl-D-arginine 1 ml of a 2.6M solution of hydrogen chloride in ether was added to a solution of 177 mg of the above described protected benzyl ester in dimethylformamide (1 ml) and the reaction mixture allowed to stand for 4 minutes at laboratory temperature. The formed hydrochloride was precipitated with ether and dried; ($E_{2.6}{}^{Gly}$=0.96, $E_{5.7}{}^{His}$=0.70).

N-Ethylpiperidine was added to a solution of hydrochloride in dimethylformamide (1 ml) in such a way that the pH was approximately 10 and a solution of 100 mg of 1-deamino-1-carbapressinoic acid (Brtnik F., Barth T., Jost K.: Collect. Czechoslovak Chem. Commun. 46, 278 (1981)) and 23 mg of N-hydroxybenzotriazole in dimethylformamide (1.5 ml) was poured into it. The reaction mixture was cooled to −30° C., and 31 mg of dicyclohexylcarbodiimide in dimethylformamide (0.5 ml) was added. Then, the mixture was stirred for 4 hours at −5° C. and for 20 hours at ambient temperature. Dicyclohexylurea was then filtered off, dimethylformamide evaporated and the residue triturated with hydrochloric acid (pH 2) and washed on a filter with water, a saturated solution of sodium hydrogencarbonate, water and ether. 160 mg of a crude product was obtained and purified by gel filtration in dimethylformamide. Effluents containing the pure compound were evaporated and the residue crystallized from dimethylformamide and water. A product of m.p. 152°–154° C. was obtained in a yield of 100 mg (60%); $[\alpha]_D -34.0°$ (c 0.45, dimethylformamide): $R_F$ 0.50 (S1), 0.54 (S3), 0.66 (S4). Analysis of amino acids: Pro 0.98, Arg 0.97, Cys($C_3H_6CO_2H$) 0.94, Gln 1.05, Asp 1.04, Tyr 0.92, Phe 1.08. For $C_{59}H_{74}N_{12}O_{14}S_2 \cdot H_2O$ (1257) calculated: 56.36% C, 6.09% H, 13.37% N, 5.10% S; found: 56.52% C, 6.13% H, 13.27% N, 5.09% S.

Preparation of the final product:

Lactam of tyrosyl-phenylalanyl-glutaminyl-asparaginyl-S-(γ-carboxypropyl)cysteinyl-prolyl-D-arginine A 30 mg solution of the above described compound in 300 μl. of trifluoroacetic acid was cooled to 0° C. Then, 200 ul. of trifluoro-methanesulfonic acid and 20 μl. of anisole were added and the mixture set aside at the same temperature for 30 minutes. The mixture was precipitated with ether and filtered through a column of anion exchanger in the acetate cycle. The effluents were freeze-dried and the lyophilizate was purified by the free-flow electrophoresis (2500 V, 135 mA).

The product of $[\alpha]_D -46°$ (c 0.1, 1M acetic acid) was obtained in the amount of 6 mg; $R_F$ 0.34 (S1), 0.57 (S4), 0.74 (S23); $E_{2.4}{}^{Gly}$ 0.80. The composition of amino acids: Arg 1.01, Pro 1.04, Gln 1.01, Asp 1.02, Phe 0.97, Tyr 0.94, Cys ($C_3H_6CO_2H$) 0.98. For $C_{45}H_{62}N_{12}O_{12}S \cdot CH_3COOH \cdot 3H_2O$ (1109) calculated: 50.89% C, 6.54% H, 15.15% N; found: 50.68% C, 6.45% H, 14.92% N.

EXAMPLE 2

Preparation of compound Ic
Preparation of starting compounds

Benzyl ester of N-benzyloxycarbonyl-S-(2,4,6-trimethylbenzyl)cysteinyl-tyrosyl-phenylalanyl-glutaminyl-asparaginyl-S-(2,4,6-trimethylbenzyl)cysteinyl-prolyl-Nδ-benzyloxycarbonalornithine. A 3M solution of hydrogen chloride in dioxane (130 μl) was added under stirring to a solution of 238 mg of the hydrazide of N-benzyl-alanyl-glutaminyl-asparaginyl-S-(2,4,6-trimethylbenzyl)cysteine (Brtnik F., Barth T., Krejci I., Jost K.: Collection Czechoslovak Chemical Communications; in press) in dimethylformamide (2 ml). The solution was cooled to −20° C. and butyl nitrite (21 mg) in dimethylformamide (0.5 ml) was added to it. The reaction mixture was stirred for 20 minutes, cooled to −40° C., neutralized with N-ethylpiperidine (pH 7 on a wet pH-indicator paper) and the solution prepared in the following manner was added:

Benzyl ester of o-nitrobenzenesulfonylprolyl-Nδ-benzyloxycarbonylornithine (Brtnik F., Barth T., Krejci I., Jost K.: Collection Czechoslovak Chemical Communications; in press) (182 mg) was dissolved in dimethylformamide (1 ml) and 3M HCl in ether (0.5 ml) was added to the solution. After 5 minutes, the reaction mixture was diluted with ether and the separated precipitate was decanted and washed with ether. The resultant hydrochloride was dissolved in dimethylformamide (2 ml), the solution adjusted with N-ethylpiperidine to a pH of 10 and the solution added to azide which preparation is described above. After 60 hours at 0° C., the reaction mixture was evaporated and the residue successively triturated with 0.5M HCl, water, a saturated solution of $NaHCO_3$ and again with water. The product was purified by crystallization from a mixture of dimethylformamide—water and by gel filtration in dimethylformamide. The product melting 238°–240° C. was obtained in the yield of 300 mg (93%), $[\alpha]_D -27.6°$ (c 0.15, dimethylformamide): $R_F$ 0.86 (S1), 0.67 (S2), 0.82 (S3), 0.91 (S4). For $C_{86}H_{103}N_{11}O_{16}S_2 \cdot 2H_2O$ (1617) calculated: 63.88% C, 6.67% H, 9.53% N, 3.97% S; found: 64.00% C, 6.38% H, 9.57% N, 3.95% S.

Preparation of the final product
[8-Ornithine, 9-desglycinamide]vasopressin 100 mg of the above-described protected octapeptide was dissolved in 1.25 ml of trifluoracetic acid, and 100 μl of thioanisol added and the solution cooled to 0° C. Trifluoromethane-sulfonic acid (1 ml) cooled to the same temperature was added into the reaction mixture. After 30 minutes at 0° C., the mixture was diluted with ether, the separated precipitate was filtered and dissolved in water (300 ml). The solution was adjusted to a pH of 6.8 with 0.1M NaOH and the reaction mixture oxidized with air oxygen for 1 hour. Then, the pH was adjusted to 3.9 with acetic acid and the solution filtered through a column of weak-basic ion exchanger in the acetate cycle. The effluents were freeze-dried (89 mg), the lyophilizate was dissolved in 50% aqueous acetic acid and the product purified by gel filtration. 15.3 mg (24%) of compound with $[\alpha]_D -15.1°$ (c 0.2, 1M acetic acid); $E_{2.4}{}^{Gly}$ 0.89, $E_{5.7}{}^{His}$ 0.34; $R_F$ 0.37 (S4), 0.43 (S13), 0.89 (S23) was obtained. Analysis of amino acids: Phe 1.01, Tyr 0.92, Gln 1.00, Asp 1.00, Pro 1.03, Orn 0.99. The amount of cystine was determined in a separate sample after oxidation with performic acid as cysteic acid: 1.92. For $C_{43}H_{59}N_{11}O_{12}S_2 \cdot 2CH_3CO_2H \cdot 2H_2O$ (1142) calculated: 49.42% C, 6.26% H, 13.48% N; found: 49.18% C, 5.95% H, 13.30% N.

EXAMPLE 3

Preparation of compound Ib
Preparation of the starting compound

Benzyl ester of N-benzyloxycarbonyl-S-(2,4,6-trimethylbenzyl)cysteinyl-tyrosyl-phenylalanyl-glutaminyl-asparaginyl-S-(2,4,6-trimethylbenzyl)cysteinyl-prolyl-$N^G$-p-toluenesolfonyl-D-arginine.

The solution of azide of protected hexapeptide was prepared in the same was as described in Example 1.

Benzyl ester of o-nitrobenzenesulfonylprolyl-$n^G$-p-toluenesulfonyl-D-arginine was prepared according to the Czechoslovak Pat. No. 8102099 (Application 2099-81). A 2M solution of hydrogen chloride in 0.5 ml of ether was added to a 200 mg solution of this compound in dimethylformamide (1 ml). The reaction mixture was allowed to stand for 5 minutes at ambient temperature and then diluted with ether. The precipitating hydrochloride was separated by suction, washed with ether, dissolved in dimethylformamide (2 ml) and the solution adjusted with N-ethyl-piperidine to a pH of 10. This solution was added to the solution of azide and the reaction mixture allowed to stand for 60 hours at 0° C. Dimethylformamide was evaporated and the residue was worked up and purified by the method described in Example 1. The product melting 230°–232° C. was obtained in the yield of 310 mg (93%): $[\alpha]_D -28.6°$ (c 0.5, dimethylformamide): $R_F$ 0.94 (S1), 0.75 (S2), 0.90 (S3), 0.96 (S4). For $C_{86}H_{105}N_{13}O_{16}S_3 \cdot H_2O$ (1691) calculated: 16.08% C, 6.26% H, 10.77% N, 5.69% S; found: 60.89% C, 6.23% H, 10.75% N, 5.42% S.

Preparation of the final product
[8-D-Arginine, 9-desglycinamide] vasopressin

The protecting groups were split from 100 mg of the abovedescribed octapeptide (100 mg) and oxidation carried out in the same way as described in Example 1. Desalting and gel filtration were also carried out. The product was obtained in a yield of 14 mg (23%); $[\alpha]_D -17.7°$ (c 0.27, 1M acetic acid); $E_{2.4}^{Gly}$ 0.56, $E_{5.7}^{His}$ 0.32; $R_F$ 0.34 (S4), 0.42 (S13), 0.91 (S23). Analysis of amino acids: Phe 1.02, Tyr 0.91, Asp 1.02, Gln 1.04, Pro 1.02, Arg 1.00, Cys (O$_3$H) 1.92 (the value for cysteic acid was obtained with a separate sample after oxidation with performic acid). For $C_{44}H_{61}N_{13}O_{12}S_2 \cdot 2CH_3COOH \cdot 1h_2O$ (1124) calculated: 49.14% C, 6.19% H, 16.20% N; found: 49.02% C, 5.98% H, 15.94% N.

We claim:

1. Analog of vasopressin of the formula

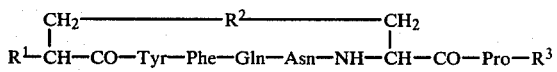

wherein $R^1$ is selected from the group consisting of H and $NH_2$, $R^2$ is selected from the group consisting of $CH_2S$ and S-S, and $R^3$ is selected from the group consisting of D-Arg and L-Orn, with all other chiral amino acids belonging to the L-series.

2. Vasopressin analog in accordance with claim 1, wherein $R^1$ is H, $R^2$ is $CH_2S$ and $R^3$ is D-Arg.

3. Vasopressin analog in accordance with claim 1, wherein $R^1$ is $NH_2$, $R^2$ is S-S and $R^3$ is D-Arg.

4. Vasopressin analog in accordance with claim 1, wherein $R^1$ is $NH_2$, $R^2$ is S-S and $R^3$ is L-Orn.

* * * * *